United States Patent [19]

Salek et al.

[11] Patent Number: 5,763,690
[45] Date of Patent: *Jun. 9, 1998

[54] MANUFACTURE OF TRIMETHYLOLPROPANE

[75] Inventors: Jeffrey S. Salek, Oakdale Borough; Joseph Pugach, Monroeville Borough; Carole L. Elias, New Kensington; Leonard A. Cullo, Greensburg, all of Pa.

[73] Assignee: Aristech Chemical Corporation, Pittsburgh, Pa.

[*] Notice: The term of this patent shall not extend beyond the expiration date of Pat. No. 5,146,012.

[21] Appl. No.: 691,760

[22] Filed: Aug. 2, 1996

Related U.S. Application Data

[63] Continuation-in-part of Ser. No. 433,584, May 3, 1995, abandoned, which is a continuation of Ser. No. 126,419, Sep. 27, 1993, abandoned, which is a continuation of Ser. No. 950,524, Sep. 25, 1992, abandoned.

[51] Int. Cl.$^6$ ........................... C07C 29/14
[52] U.S. Cl. .............. 568/853; 568/863; 568/881
[58] Field of Search ............... 568/853, 863, 568/881

[56] References Cited

U.S. PATENT DOCUMENTS 4,122,290  10/1978  Immel et al. .
4,855,515   8/1989  Morris et al. .

Primary Examiner—Rebecca Cook
Attorney, Agent, or Firm—Robert R. Gavlik, Esq.

[57] ABSTRACT

Trimethylolpropane of high purity is efficiently made by mixing the aldol reaction product of formaldehyde and n-butyraldehyde with at least about 20 wt % of a lower alcohol prior to hydrogenation. The alcohol addition also promotes hydrogenolysis of by-product esters at pressures below 3000 psig and allows recovery of high purity product by simple distillation.

13 Claims, No Drawings

MANUFACTURE OF TRIMETHYLOLPROPANE

RELATED APPLICATIONS

This application is a continuation-in-part of our application Ser. No. 433,584, filed May 3, 1995 abandoned, which is a continuation of application Ser. No. 126,419, filed Sep. 27, 1993, now abandoned, which is a continuation of application Ser. No. 950,524, filed Sep. 25, 1992, abandoned.

TECHNICAL FIELD

This invention relates to the production of trimethylolpropane sometimes referred to herein as "TMP" and particularly to conducting the hydrogenation of the reaction product of n-butyraldehyde (NBAL) and formaldehyde and hydrogenolysis of ester impurities, and in the presence of at least 20% of a lower alcohol of the formula $R^1R^2CHOH$ where $R^1$ and $R^2$ are independently hydrogen or alkyl groups having 1 to about 5 carbon atoms but together have no more than 6 carbon atoms.

BACKGROUND OF THE INVENTION

The conventional production of trimethylolpropane typically entails the reaction of n-butyraldehyde and formaldehyde (usually an aqueous solution) to obtain the aldol reaction product which may then be hydrogenated over a hydrogenation catalyst either with or without treatment intended to purify it. Representative of the prior art are U.S. Pat. Nos. 4,122,290 and 4,514,578 to Immel et al and 4,594,461 to Merger et al, which may use a trialkyl-amine catalyst in the aldol step. While the conventional commercial processes have served more or less satisfactorily in the context of the state of the art, our process is much more efficient and the product is much more pure.

Commercially, formaldehyde is available in either of two forms, paraformaldehyde or as an aqueous solution (referred to herein as aqueous formaldehyde). Paraformaldehyde is a crystalline solid consisting of a linear polymeric form of formaldehyde of the molecular formula, $HO(CH_2)_nH$ where n=8–100. Aqueous formaldehyde consists predominantly as formaldehyde in its monomeric form. On standing, it will gradually react with itself forming oligomeric formaldehyde and paraformaldehyde. This is commonly inhibited by adding up to 15% methanol as a stabilizer. Where "formaldehyde" is used hereafter, we mean that either formaldehyde in the form of paraformaldehyde or aqueous formaldehyde is acceptable unless otherwise specified.

Klein, in U.S. Pat. No. 3,076,854, treats a crude trimethylolpropane by solvent extracting with an alcohol such as amyl alcohol, re-extracting with water, heating with methanol in the presence of a strong acid, and passing through an ion exchange bed to remove metals. Purification was not accomplished by distillation as in the present invention.

In East German Patent 142,184, Dietze et al follow a more or less conventional TMP preparation by distillation to obtain a distillation bottoms comprising about 3% of the reaction product; this bottoms portion is treated with methanol and passed through a strong acid resin to liberate additional TMP.

Merger et al, in European Patent 289,921, treat the hydrogenated effluent of the trialkylamine catalyzed reaction of n-butyraldehyde and aqueous formaldehyde in one of two ways. In the first they remove water and excess trialkylamine by distillation at 100°–200° C. Trialkylamine which is tied up as its formate salt reacts with trimethylolalkane under distillation conditions to give free trialkylamine and formate esters of the polyol. They then add methanol and either an alcoholate of an alkalai or alkaline earth metal to liberate the trimethylolalkane which is recovered by distillation. The second method involves removal of the excess water and free trialkylamine by distillation followed by the addition of methanol to the distillation bottoms. This mixture is then heated to 100°–200° C. under pressure, and trialkylamine and methyl formate are removed by distillation. The water concentration in this instance is quite stringent and can be no more than 5–15%. While the product is finally recovered by distillation, no mention is made of purity. Our process does not require any special treatment before alcohol addition and leads to a product of very high purity.

Raue et al, in Example 1 of East German Patent 273,434, describe a process for recovering formaldehyde from the $Ca(OH)_2$ catalyzed reaction of higher aldehydes with formaldehyde to form polymethylolalkanes. The treatment first requires neutralization of the reaction effluent followed by addition of methanol, stripping of lights at 50° C. under vacuum, treating with acetonitrile, removing calcium salts, adding additional methanol and stripping up to 90° C. to remove lights including formaldehyde. No mention is made of product recovery. Our process is simple, different, and leads to high purity TMP.

Immel et al, in U.S. Pat. No. 4,122,290, disclose a process for preparing trimethylolalkanes by the aldol reaction of similar starting materials compared to the present invention. However, Immel does not disclose the addition of alcohol prior to hydrogenation to promote hydrogenolysis at low pressures; that is, at pressures below 3000 psig. A surprising feature of the present invention is that hydrogenolysis will occur at pressures as low as 500 psig.

SUMMARY OF THE INVENTION

Our process involves an aldol reaction of n-butyraldehyde and formaldehyde followed directly by a hydrogenation step conducted in the presence of at least about 20% by weight lower alcohol of the formula $R^1R^2CHOH$ where $R^1$ and $R^2$ are independently hydrogen or alkyl groups having 1 to about 5 carbon atoms but together have no more than 6 carbon atoms. In the hydrogenation step the catalyst, preferably copper chromite, is used at temperatures in the range of about 100° C. to about 200° C., and relatively low pressures, in the range of 500 to about 3000 psig. Preferably, the pressure is 500 to 2500 psig, more preferably 500 to 2000 psig, and most preferably 500 to 1000 psig. Our invention will give good yields of desired product, having very high purity, as will become apparent in the section below.

To make the hydrogenation feed, the n-butyraldehyde and the formaldehyde should be employed in molar ratios of about 0.5 to about 10, preferably 0.5 to 5 and most preferably about 1 to about 2.5.

We prefer to use a hydrogenation feed containing 20 to 90% alcohol, preferably 30–60% alcohol, and most preferably 50% alcohol; the preferred alcohol is methanol. By adding the alcohol prior to hydrogenation, low pressure hydrogenolysis is promoted. Typically, reaction ester impurity hydrogenolysis occurs only at 3000 psig and above. The present invention has the unexpected feature of promoting hydrogenolysis at pressures as low as about 500 psig.

DETAILED DESCRIPTION OF THE INVENTION

Our invention will be described with particular attention to the examples below.

Specific Procedure using Paraformaldehyde

A specific reaction using paraformaldehyde may be described as follows: The reaction is performed in a reflux apparatus wherein 1.00 equivalent of NBAL, 2.50 equivalents of paraformaldehyde, and about 0.04 to 0.05 equivalents of triethylamine have been placed under an inert atmosphere. With overhead stirring, the reaction mixture is heated, initially, in a water bath at 50° C.; the temperature is gradually increased to 80° C. over a one-hour period. The reaction is continued for an additional hour and terminated. The clear molten liquid is diluted in an alcohol, preferably methanol, and hydrogenated by passing the reaction solution over a conventional copper chromite catalyst at about 160° C. and about 1000 psi $H_2$. High purity TMP product (>99%) is recovered in good yield by distillation.

Specific Procedure using Aqueous Formaldehyde

Another specific reaction using aqueous formaldehyde may be described as follows: The reaction is performed in a reflux apparatus wherein 1.00 equivalent of NBAL, 2.50 equivalents of aqueous formaldehyde, and about 0.04 to 0.08 equivalents of triethylamine have been placed under an inert atmosphere. Preferably the NBAL is added dropwise over a 0.25–1 hour period to the stirred mixture of aqueous formaldehyde and triethylamine. With overhead stirring, the reaction mixture is heated in a water bath at 60° C. for two hours. The clear liquid is diluted in an alcohol preferably methanol and hydrogenated by passing the reaction solution over a conventional copper chromite catalyst at about 160° C. and about 1000 psi. High purity TMP product (>99%) is recovered in good yield by distillation.

General Procedure using Formaldehyde

More generally, with 1 equivalent of NBAL we may place in a reaction vessel from about 2 to about 10 equivalents of formaldehyde and about 0.001 to about 1.0 (preferably about 0.05 to about 0.5) equivalent of a tertiary amine catalyst. The reaction mixture is stirred at 60°–80° C. until most of the NBAL is consumed. The resulting solution is diluted in an alcohol preferably methanol and hydrogenated using a hydrogenation catalyst. High purity TMP product is obtained in good yield by distillation.

EXAMPLE 1

A series of batch aldol reactions were performed in glassware as follows:

A. n-Butyraldehyde (1069.3 g, 14.89 mol), paraformaldehyde (1223.4 g, 37.07 mol), water (132.4 g, 7.35 mol), and triethylamine (75.0 g, 0.74 mol) were added into a 3-neck roundbottom flask equipped with an overhead stirrer, inert atmosphere purge, and a reflux condenser. The apparatus was placed in a water bath at 50° C. The bath was heated to a temperature of 80° C. over a period of 2 hours at which point >99% of the n-butyraldehyde was reacted. The reaction mixture was diluted in methanol to make a 50 wt % aldol in methanol solution. A continuous hydrogenation was performed by passing the methanolic aldol effluent upward through a fixed-bed of copper chromite at 160° C., 0.5 $hr^{-1}$ liquid hour space velocity (LHSV), and 1000 psig $H_2$. The resultant hydrogenation product was batch distilled using an 8-inch long packed column to recover high purity trimethylolpropane product (99.18% purity, 73.3% recovery).

B. n-Butyraldehyde (643.7 g, 8.93 mol), aqueous formaldehyde (1811.2 g, 22.32 mol), and triethylamine (45.2 g, 0.45 mol) were added into a 3-neck roundbottom flask equipped with an overhead stirrer, inert atmosphere purge, and a reflux condenser. The apparatus was lowered into a water bath at 40° C. The bath was heated to a temperature of 60° C. over a period of 1 hour and continued for an additional hour at which point 97% of the n-butyraldehyde was reacted. The reaction mixture was diluted in methanol to make a 50 wt % aldol in methanol solution. A continuous hydrogenation was performed by passing the methanolic aldol effluent upward through a fixed-bed of stabilized copper chromite at 160° C., 0.5 $hr^{-1}$ LHSV, and 1000 psig $H_2$. The resultant hydrogenation product was batch distilled using an 8-inch long packed column to recover high purity trimethylolpropane product (99.07% purity, 68.4% recovery).

C. Example 1.A. was repeated except that the aldol reaction mixture was diluted in n-butyl alcohol rather than methanol to make a 50 wt % aldol in n-butyl alcohol solution. High purity trimethylolpropane product was obtained (99.15% purity, 72.3% recovery).

D. The "control" experiment was performed by repeating Example 1.B. without adding the methanol solvent prior to hydrogenation. The trimethylolpropane product recovered was of lower purity (98.33% purity, 73.0% recovery).

The data for these four experiments are summarized in Table I. The results reveal the surprising improvement in trimethylolpropane purity made possible by the addition of a suitable alcohol solvent to aldol reaction product prior to hydrogenation.

Table I

| Example | 1A. | 1B. | 1C. | 1D. ("control") |
| --- | --- | --- | --- | --- |
| HCHO Type | paraformaldehyde | aqueous formaldehyde | paraformaldehyde | aqueous formaldehyde |
| Added Solvent | methanol | methanol | n-butyl alcohol | none |
| Solvent Level (wt %) | 50% | 50% | 50% | 5% (contained) |
| Distilled TMP Purity (wt %) | 99.18% | 99.07% | 99.15% | 98.33% |
| TMP Recovery | 73% | 68% | 72% | 73% |

EXAMPLE 2

Two batch aldol reactions were performed in glassware as follows:

A. n-Butyraldehyde (772.4 g, 10.71 mol), aqueous formaldehyde (2173.4 g, 26.78 mol), and triethylamine (54.2 g, 0.54 mol) were added into a 3-neck roundbottom flask equipped with an overhead stirrer, inert atmosphere purge, and a reflux condenser. The apparatus was lowered into a water bath at 40° C. The bath was heated to a temperature of 60° C. over a period of 2 hours at which point >99% of the n-butyraldehyde was reacted. The reaction mixture was diluted in methanol to make a 90 wt % methanol solution. A continuous hydrogenation was performed by passing the methanolic aldol effluent upward through a fixed-bed of stabilized copper chromite at 160° C., 0.5 $hr^{-1}$ LHSV, and 1000 psig $H_2$. The resultant hydrogenation product was batch distilled using an 8-inch long packed column to recover high purity trimethylolpropane product (99.02% purity, 66% recovery).

B. n-Butyraldehyde (943.4 g, 13.08 mol), paraformaldehyde (1079.3 g, 33.71 mol), water (116.8 g, 6.48 mol) and triethylamine (66.2 g, 0.65 mol) were added into a 3-neck roundbottom flask equipped with an overhead stirrer, inert atmosphere purge, and a reflux condenser. The apparatus was lowered into a water bath at 50° C. The bath was heated to a temperature of 80° C. over a period of 1 hour and continued for an additional hour at which point 99% of the n-butyraldehyde was reacted. The reaction mixture was diluted in methanol to make a 20 wt % methanol solution. A continuous hydrogenation was performed by passing the methanolic aldol effluent upward through a fixed-bed of stabilized copper chromite at 160° C., 0.5 hr$^{-1}$ LHSV, and 1000 psig H$_2$. The resultant hydrogenation product was batch distilled using an 8-inch long packed column to recover high purity trimethylolpropane product (99.01% purity, 91% recovery).

The data for these two experiments, when compared to Example 1A. and Example 1B., show similar TMP distilled purities (>99%) in good recoveries using higher (90 wt %) and lower (20 wt %) methanol levels. These results are displayed in Table II.

TABLE II

| Example | 1A. | 1B. | 2A. | 2B. |
|---|---|---|---|---|
| HCHO Type | paraform-aldehyde | aqueous formaldehyde | aqueous formaldehyde | paraform-aldehyde |
| Added Solvent | methanol | methanol | methanol | methanol |
| Solvent Level (wt %) | 50% | 50% | 90% | 20% |
| Distilled TMP Purity (wt %) | 99.18% | 99.07% | 99.02% | 99.01% |
| TMP Recovery | 73% | 68% | 66% | 91% |

EXAMPLE 3

A batch aldol reaction was performed in glassware as follows:

n-Butyraldehyde (600.0 g, 8.32 mol), paraformaldehyde (686.4 g, 20.80 mol), water (74.31 g, 4.12 mol), and triethylamine (42.1 g, 0.42 mol) were added into a 3-neck roundbottom flask equipped with an overhead stirrer, inert atmosphere purge, and a reflux condenser. The apparatus was lowered into a water bath at 50° C. The bath was heated to a temperature of 80° C. over a period of 2 hours at which point 99% of the n-butyraldehyde was reacted. The reaction mixture was diluted to make a 50 wt % aldol in 2-methyl-1-butanol solution. A continuous hydrogenation was performed by passing the aldol effluent upward through a fixed-bed of stabilized copper chromite at 160° C., 0.5 hr$^{-1}$ LHSV, and 1000 psig H$_2$. The resultant hydrogenation product was batch distilled using an 8-inch long packed column to recover high purity trimethylolpropane product (99.49% purity, 72% recovery).

The results obtained from this experiment, when compared to Example 1A., show similar distilled TMP purity and recovery using a different indigenous alcoholic solvent, 2-methyl-1-butanol (Table III).

TABLE III

| Example | 1A. | 3. |
|---|---|---|
| HCHO Type | paraform-aldehyde | paraform-aldehyde |
| Added Solvent | methanol | 2-methyl-1-butanol |
| Solvent Level (wt %) | 50% | 50% |
| Distilled TMP Purity (wt %) | 99.18% | 99.49% |
| TMP Recovery | 73% | 72% |

EXAMPLE 4

A batch aldol reaction was performed in glassware as follows:

n-Butyraldehyde (772.4 g, 10.71 mol), aqueous formaldehyde (2173.4 g, 26.78 mol), and triethylamine (54.2 g, 0.54 mol) were added into a 3-neck roundbottom flask equipped with an overhead stirrer, inert atmosphere purge, and a reflux condenser. The apparatus was lowered into a water bath at 40° C. The bath was heated to a temperature of 60° C. over a period of 2 hours at which point >99% of the n-butyraldehyde was reacted. A continuous hydrogenation was performed by passing the undiluted aldol effluent upward through a fixed-bed of stabilized copper chromite at 160° C., 0.5 hr$^{-1}$ LHSV, and 1000 psig H$_2$. The resultant hydrogenation product was diluted in methanol to make a 50 wt % solution and batch distilled using an 8-inch long packed column to recover trimethylolpropane product (98.92% purity, 68% recovery).

The result obtained from this experiment, when compared to Example 1D., (the "control" experiment using alcoholic solvent was not added prior to hydrogenation or distillation), shows an improved distilled TMP purity at a similar recovery. However, the product purity was not quite as high when the alcoholic solvent was added to the aldol effluent prior to hydrogenation (such as shown in Example 1A. or Example 3.) which is our most preferred mode. These results are displayed together in Table IV.

TABLE IV

| Example | 1A. | 1D. ("control") | 3. | 4. |
|---|---|---|---|---|
| HCHO Type | paraform-aldehyde | aqueous formaldehyde | paraform-aldehyde | aqueous formaldehyde |
| Added Solvent | methanol | none | 2-methyl-1-butanol | methanol (after hydrogenation) |
| Solvent Level (wt %) | 50% | 5% (contained) | 50% | 50% (after hydrogenation) |
| Distilled TMP Purity (wt %) | 99.18% | 98.33% | 99.49% | 98.92% |
| TMP Recovery | 73% | 73% | 72% | 68% |

EXAMPLE 5

A batch aldol reaction was performed in glassware as follows:

n-Butyraldehyde (960.0 g, 13.31 mol), paraformaldehyde (1098.3 g, 33.28 mol), water (111.3 g, 6.17 mol) and triethylamine (67.4 g, 0.67 mol) were added into a 3-neck roundbottom flask equipped with an overhead stirrer, inert atmosphere purge, and a reflux condenser. The apparatus was lowered into a water bath at 50° C. The bath was heated to a temperature of 80° C. over a period of 1 hour and continued for an additional hour at which point 98% of the n-butyraldehyde was reacted. The reaction mixture was diluted in isopropyl alcohol (IPA) to make a 50 wt % solution. A continuous hydrogenation was performed by passing the methanolic aldol effluent upward through a fixed-bed of stabilized copper chromite at 160° C., 0.5 hr$^{-1}$ LHSV, and 1000 psig $H_2$. The resultant hydrogenation product was batch distilled using an 8-inch long packed column to recover high purity trimethylolpropane product (99.29% purity, 70% recovery).

The data for this experiment, when compared to Example 1A. and Example 1B., show similar TMP distilled purities (>99%) in good recoveries using a 2° alcohol as solvent. These results are shown in Table V.

TABLE V

| Example | 1A. | 1B. | V. |
|---|---|---|---|
| HCHO Type | paraformaldehyde | aqueous formaldehyde | paraformaldehyde |
| Added Solvent | methanol | methanol | isopropyl alcohol |
| Solvent Level (wt %) | 50% | 50% | 50% |
| Distilled TMP Purity (wt %) | 99.18% | 99.07% | 99.29% |
| TMP Recovery | 73% | 68% | 70% |

We claim:

1. Method of making trimethylolpropane comprising the steps of:
   (a) reacting n-butyraldehyde and formaldehyde under aldol reaction conditions to form a reaction product comprising said trimethylolpropane and at least one ester impurity;
   (b) hydrogenating the reaction product at a pressure of about 500–3000 psig, and in the presence of a copper chromite catalyst and an alcohol having the formula $R^1R^2CHOH$, wherein $R^1$ and $R^2$ are each independently an hydrogen or an alkyl group having one to five carbon atoms, and wherein the total of the carbon atoms in both $R^1$ and $R^2$ is no more than six, and wherein said alcohol is at least 20 wt % of said alcohol and said reaction product; and
   (c) hydrogenolyzing said ester impurity in the presence of said alcohol and said catalyst.

2. Method of claim 1 wherein the hydrogenation is conducted at a pressure in the range of about 500 to about 2500 psig.

3. Method of claim 1 wherein the hydrogenation is conducted at a pressure of about 500 to 2000 psig.

4. Method of claim 1 wherein the hydrogenation is conducted at a pressure in the range of 500 to 1000 psig.

5. Method of claim 1 wherein the alcohol comprises methanol.

6. Method of claim 1 wherein the aldol reaction step is conducted in the presence of a catalyst comprising an amine of the formula $R^1R^2R^3N$ wherein $R^1$, $R^2$, and $R^3$ are each independently an alkyl or an aryl group having from 1 to 5 carbon atoms and wherein $R^1$ and $R^2$ may form a substituted or unsubstituted cyclic group having about 5 to about 10 carbon atoms.

7. Method of claim 6 wherein the aldol reaction step is conducted in the presence of a triethylamine catalyst.

8. Method of claim 1 wherein the formaldehyde is in the form of paraformaldehyde.

9. Method of claim 1 wherein the formaldehyde is in the form of aqueous formaldehyde.

10. Method of claim 1 wherein trimethylolpropane of greater than 99% purity is recovered by distillation.

11. Method of claim 1 wherein the hydrogenation step is conducted at a temperature of about 100° C. to about 200° C.

12. Method of claim 1 wherein the molar ratio of n-butyraldehyde to formaldehyde in the aldol reaction is about 1:2 to about 1:5.

13. Method of claim 5 wherein the methanol is present in an amount from about 30% to about 60% of the hydrogenation feed.

* * * * *